(12) United States Patent
Lacy et al.

(10) Patent No.: US 11,213,437 B2
(45) Date of Patent: Jan. 4, 2022

(54) DISPOSABLE ABSORBENT ARTICLES

(71) Applicant: The Procter & Gamble Company, Cincinnati, OH (US)

(72) Inventors: Lauren Jane Lacy, Cincinnati, OH (US); Amit Kaushik, West Chester, OH (US); Emma Lynn Sartini, Covington, KY (US); Matthew Steven Ritter, Liberty Township, OH (US); Andrew Saska, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 460 days.

(21) Appl. No.: 16/164,838

(22) Filed: Oct. 19, 2018

(65) Prior Publication Data

US 2019/0117479 A1 Apr. 25, 2019

Related U.S. Application Data

(60) Provisional application No. 62/574,876, filed on Oct. 20, 2017.

(51) Int. Cl.
| | | |
|---|---|---|
| *A61F 13/15* | (2006.01) | |
| *A61F 13/538* | (2006.01) | |
| *A61F 13/472* | (2006.01) | |
| *A61F 13/551* | (2006.01) | |
| *A61F 13/53* | (2006.01) | |

(52) U.S. Cl.
CPC ......... *A61F 13/538* (2013.01); *A61F 13/472* (2013.01); *A61F 13/47236* (2013.01); *A61F 13/47245* (2013.01); *A61F 13/55145* (2013.01); *A61F 2013/530802* (2013.01)

(58) Field of Classification Search
CPC .. A61F 13/538; A61F 13/472; A61F 13/4726; A61F 13/47245; A61F 13/55145; A61F 2013/530802

See application file for complete search history.

(56) References Cited

U.S. PATENT DOCUMENTS

| | | | |
|---|---|---|---|
| 3,570,491 A | 3/1971 | Sneider | |
| 2004/0068247 A1 | 4/2004 | Connor | |
| 2005/0065492 A1* | 3/2005 | Cole | A61F 13/15577 604/385.01 |
| 2007/0135788 A1 | 6/2007 | Damay | |
| 2013/0165886 A1* | 6/2013 | Glaug | A61F 13/4946 604/385.01 |
| 2016/0038353 A1 | 2/2016 | Bonilla et al. | |
| 2017/0071798 A1* | 3/2017 | Horle | A61F 13/15804 |
| 2017/0071799 A1 | 3/2017 | Hörle et al. | |

FOREIGN PATENT DOCUMENTS

KR 2010002767 * 1/2010 ............. A61F 13/15

OTHER PUBLICATIONS

International Search Report and Written Opinion for PCT/US2018/056044 dated Jan. 7, 2019.

* cited by examiner

*Primary Examiner* — Jacqueline F Stephens
(74) *Attorney, Agent, or Firm* — George H. Leal

(57) ABSTRACT

An array of disposable absorbent articles is described herein. The array has a first plurality of absorbent articles and a second plurality of absorbent articles. Each of the first plurality and second plurality of absorbent articles have absorbent cores having patterned end edges each having a plurality of inflection points.

14 Claims, 13 Drawing Sheets

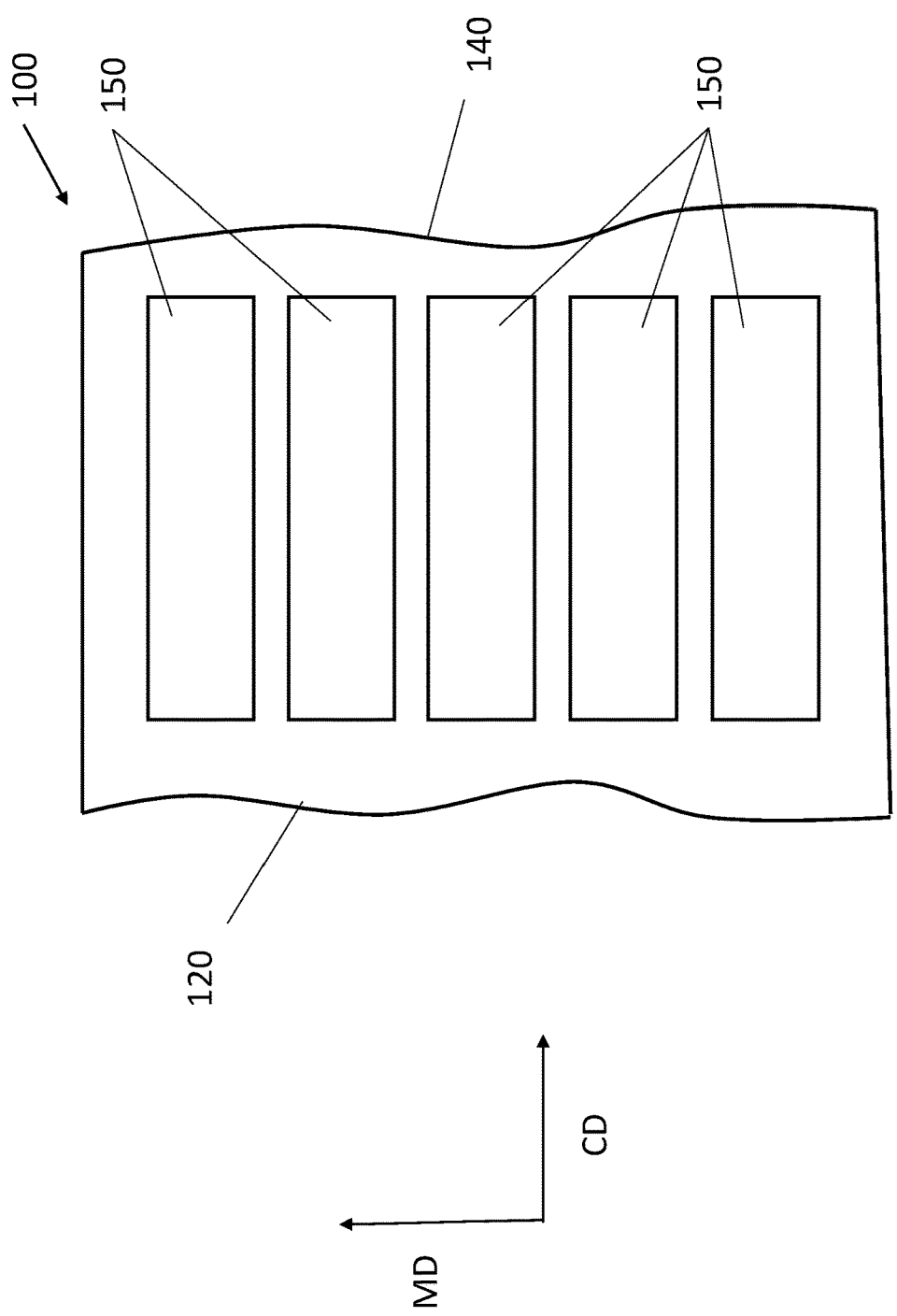

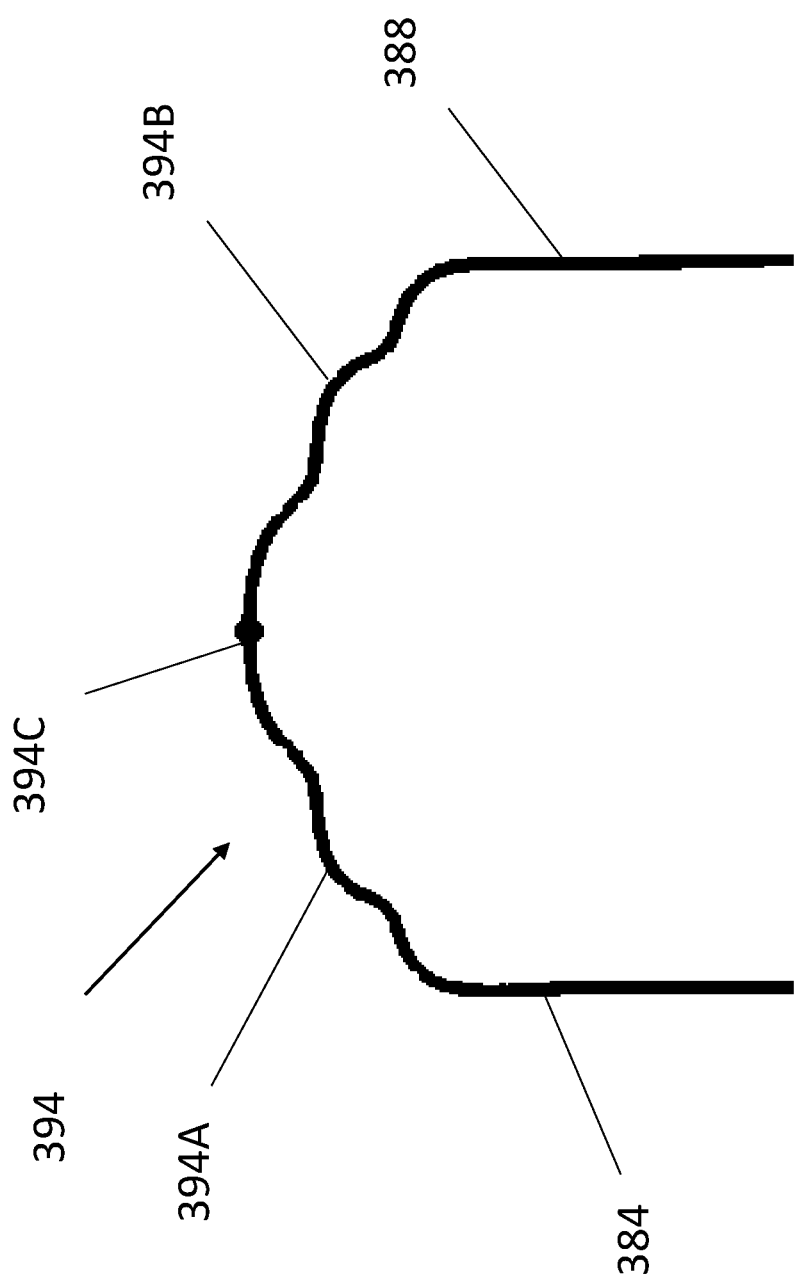

DISPOSABLE ABSORBENT ARTICLES

FIELD OF THE INVENTION

The present invention pertains to disposable absorbent articles, particularly, disposable absorbent articles having variable length absorbent cores.

BACKGROUND OF THE INVENTION

Disposable absorbent articles are widely used to absorb bodily fluid insults. In general, disposable absorbent articles comprise a plurality of layers providing specific functions in absorbing and retaining fluid insults. Each of the plurality of layers are often provided as rolled webs of material which are unrolled and assembled during processing.

There are a number of complexities which may arise during the processing of disposable absorbent articles. For example, the rolled webs of material may have variable widths in a cross machine direction. Additionally, during processing, the webs of material may mis-track (shift) in a cross machine direction. Moreover, the rolled webs of material can shift in a machine direction depending on the tension applied during processing; the web material mechanical behavior and/or the web caliper/thickness changes.

The variable width of a material web can be an important factor where the edges of the web are expected to form an internal or external edge of the resultant absorbent article. Due to the variability of width of the material webs utilized, the utilization of the edges of the web to create edges of the components of the product is generally discouraged. As an example, the utilization of the edges of material webs for topsheets and backsheets can create negative consumer sentiment due to the non-uniform sizes of articles within a single package. Similarly, the edges of the material webs for those components disposed between the topsheet and backsheet may be utilized, e.g. absorbent core, secondary topsheets. However, the variability of the width of these material webs can be equally as visually unappealing to a user as the non-uniform sizes of the article mentioned previously. Such non-uniformity may provide an indication of low quality to the consumer and ultimately erode brand equity.

To avoid this issue, the final shapes of, for example, a topsheet and a backsheet, are cut out of their respective material webs such that the web edges do not form a part of the resultant article. Similarly, components sandwiched between the topsheet and backsheet may similarly be cut such that their respective material webs' edges are not utilized for any internal edges of the absorbent article. Unfortunately, while this practice creates uniformly shaped components for absorbent articles, such processing can lead to a large amount of scrap material which in turn means a loss of revenue.

Based on the foregoing, what is needed is a process for creating absorbent articles which minimizes the creation of scrap material. And, what is also needed are articles that incorporate components which utilize material web edges in their finished state.

SUMMARY OF THE INVENTION

The absorbent articles of the present invention, can reduce the amount of waste produced from creating discrete absorbent cores from an absorbent core web. In some particular forms, an array of absorbent articles may comprise: a first plurality of absorbent articles and a second plurality of absorbent articles, each of the first plurality of absorbent articles and the second plurality of absorbent articles comprising a topsheet; a backsheet; and an absorbent core disposed between the topsheet and the backsheet, wherein, each absorbent core has a first longitudinal side edge and a second longitudinal side edge, a first end edge connecting the first longitudinal side edge and the second longitudinal side edge on one end of the absorbent core, a second end edge connecting the first longitudinal side edge and the second longitudinal side edge on an opposing second end of the absorbent core, wherein each of the first end edge and the second end edge comprise a first patterned portion, a second patterned portion, and a connecting portion, wherein each of the first patterned portion and second pattern portion comprise a plurality of inflection points as determined via the k-curvature analysis test method, wherein a first portion of absorbent cores is associated with the first plurality of absorbent articles and wherein each of the absorbent cores of the first portion has a first length and a second portion of absorbent cores is associated with the second plurality of absorbent articles and wherein each of the absorbent cores of the second portion has a second length, and wherein the first length and second length are different.

BRIEF DESCRIPTION OF THE DRAWINGS

The above-mentioned and other features and advantages of the present disclosure, and the manner of attaining them, will become more apparent and the disclosure itself will be better understood by reference to the following description of example forms of the disclosure taken in conjunction with the accompanying drawings.

FIG. 1B is a plan view showing a conventional absorbent web from which discrete absorbent cores are created.

FIG. 3C is a close up view showing a first end of the discrete absorbent core of FIG. 3A encircled as 3C.

DETAILED DESCRIPTION OF THE INVENTION

The disposable absorbent articles described herein comprise variably dimensioned components positioned between the topsheets and backsheets of their respective absorbent articles. The components are contoured such that any negative visual impact by the variability in dimensions is reduced. Additionally, the processes described herein allows for the creation of discrete portions of a material web which are variably dimensioned.

As used herein, "disposable absorbent article" or "absorbent article" refers to a feminine sanitary pads, baby diapers, baby pants, adult incontinence products, adult incontinence pads, or the like. For the sake of facility, reference shall be made to feminine sanitary napkins despite the applicability of the present invention to other absorbent articles described herein.

Figure 1A:
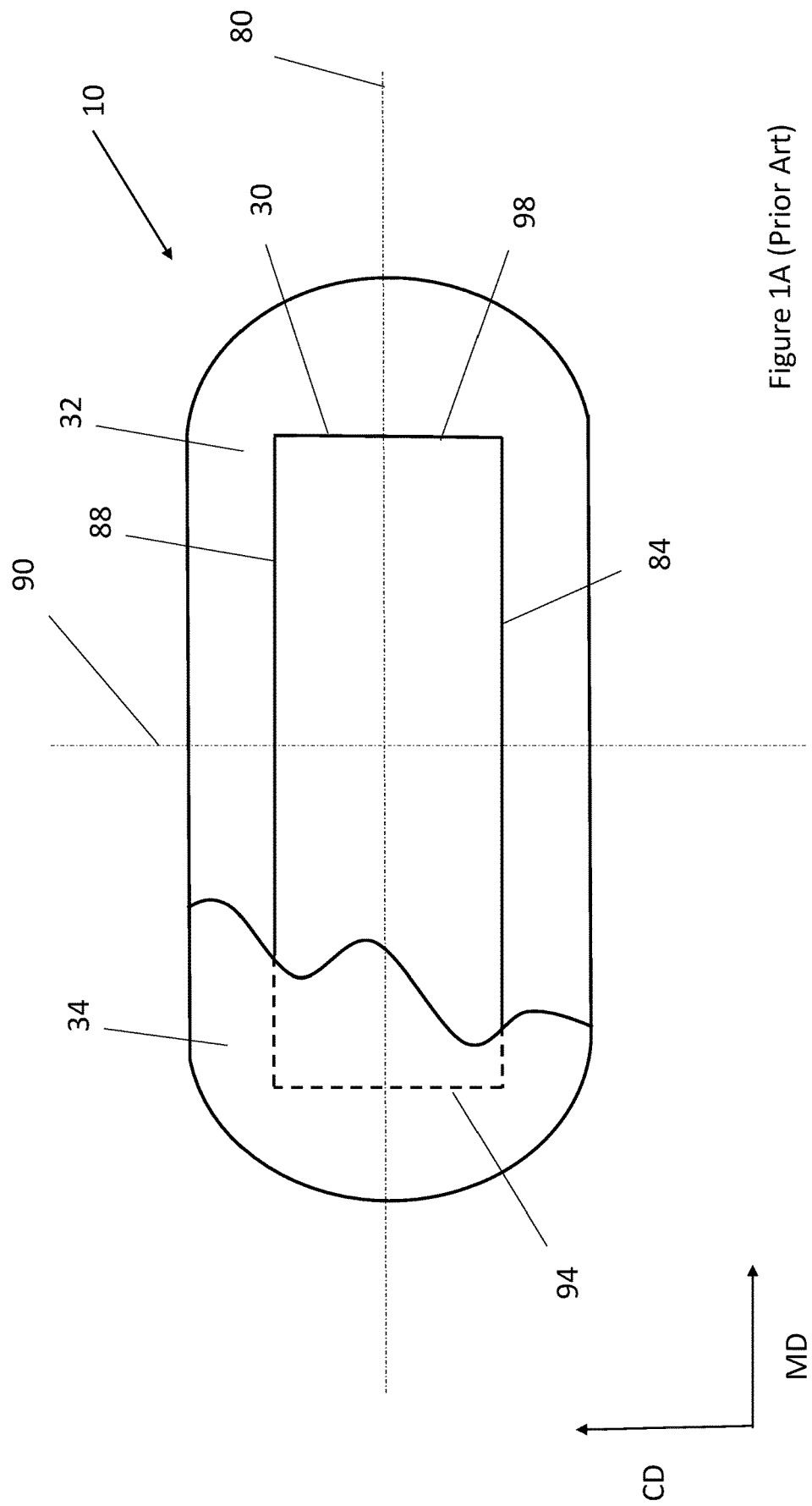
FIG. 1A is a plan view showing a conventional feminine sanitary pad.

Referring to FIG. 1A, a conventional sanitary pad 10 is shown. The pad 10 comprises a longitudinal centerline 80 and a lateral centerline 90 which is perpendicular to the longitudinal centerline 80 and in the same plane as the pad 10 in a flattened state. The longitudinal centerline 80 being generally parallel with a machine direction "MD," and the lateral centerline 90 being generally parallel with a cross-machine direction "CD." The sanitary pad 10 further comprises a topsheet 34, a backsheet 32, and an absorbent core 30 disposed between the topsheet 34 and the backsheet 32.

The absorbent core 30 comprises a first longitudinal side edge 84 and a second longitudinal side edge 88, each being generally parallel with the longitudinal centerline 80. A first end edge 94 connects the first longitudinal side edge 84 and the second longitudinal side edge 88 on one end of the sanitary pad 10. Each of the first end edge 94 and the second end edge 98 being generally parallel to the lateral centerline 90. A second end edge 98 connects the first longitudinal side edge 84 and the second longitudinal side edge 88 on an opposite end of the sanitary pad 10.

A conventional absorbent core web 100 is shown in FIG. 1B. The conventional absorbent core web 100 comprises a first web edge 120 and a second web edge 140. A plurality of discrete absorbent cores 150 are highlighted for convenience on the absorbent core web 100. To avoid the variability of the length of the discrete absorbent cores, the discrete absorbent cores 150 shown are completely cut out of the absorbent core web material 100 such that the first web edge 120 and the second web edge 140 do not form any edges of the discrete absorbent cores 150. But, as noted previously, this can create much scrap material in the way of the absorbent core web material.

Figure 2A:
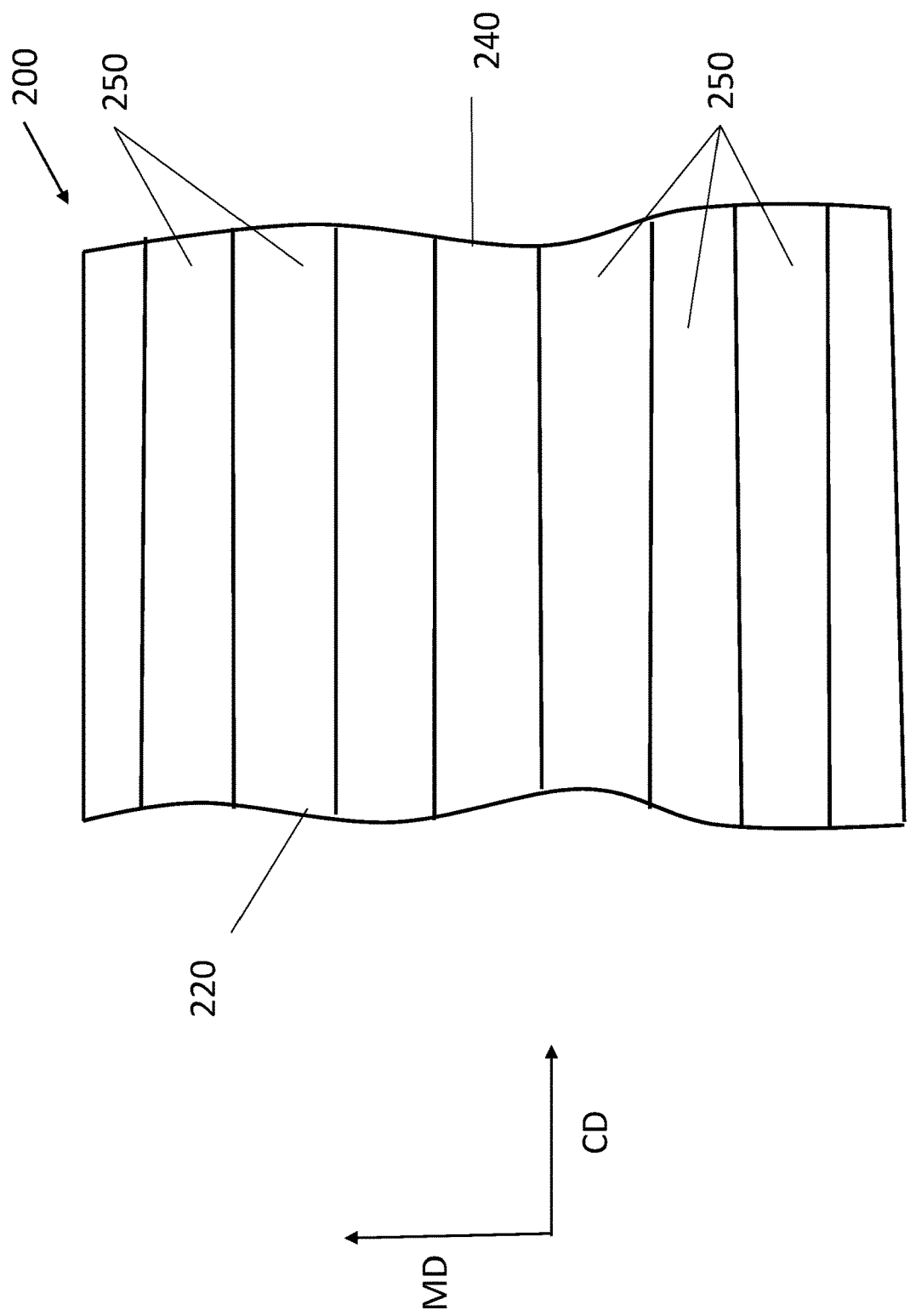
FIG. 2A is a plan view showing an absorbent web in accordance with the present disclosure.

Referring now to FIG. 2A, in contrast to the processing of the absorbent core web 100 as described with regard to FIG. 1B, an absorbent core web 200, of the present disclosure may be processed such that discrete cores 250 include at least a portion of a first web edge 220 and at least a portion of a second web edge 240 of the absorbent core web 200. The first web edge 220 and the second web edge 240 are exaggerated and shown as wavy to ease visualization of the variable dimensioned absorbent cores.

However, in many instances, the first web edge 220 and the second web edge 240 have a variable distance there between but the variability may be subtle. So, in many instances the first web edge 220 and second web edge 240 are simply not always straight. Because the first web edge 220 and the second web edge 240 are not always straight, the discrete absorbent cores 250 derived from the web have variable dimensions, particularly the length (generally parallel to the CD) as shown.

It is worth noting that forms of the present disclosure are contemplated where the length dimension of the discrete absorbent cores are oriented in the MD. In such forms, a width of the discrete absorbent cores may be impacted by non-straight absorbent core web edges. Additionally, in such forms, the width of the discrete absorbent cores may then be variable to some extent as discussed below with regard to the lengths of the absorbent cores. And, while the discussion below pertains to variable lengths and modifications to mitigate the negative appearance of the variable lengths, similar modifications may be provided to mitigate the negative appearance of variable widths of absorbent cores as needed.

Figure 2B:
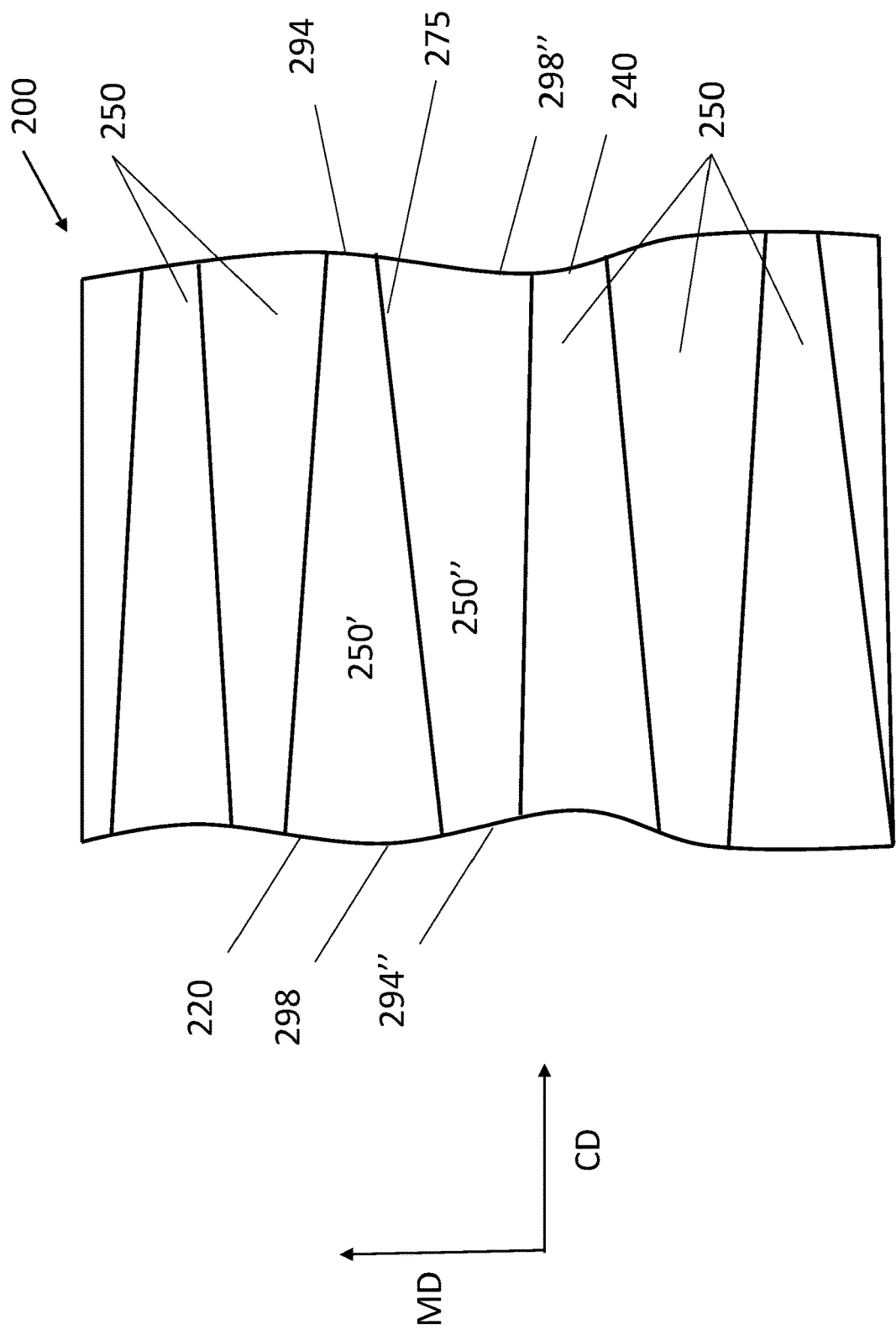
FIG. 2B is a plan view showing another version of the absorbent web in accordance with the present disclosure.

In some forms, as shown in FIG. 2B, the discrete cores 250 may be nested. For example, a discrete absorbent core 250' may comprise a first edge 294 which comprise a portion of the second web edge 240 and the second edge 298 of the discrete absorbent core 250' may comprise a portion of the first web edge 220. As shown, an adjacent discrete absorbent core 250" may comprise a first edge 294" which comprises a portion of the first web edge 220. Additionally, the discrete absorbent core 250" may comprise a second edge 298" which comprises a portion of the second web edge 240. And as shown, the discrete absorbent cores 250' and 250" may share a common edge 275. As shown, the absorbent cores 250' and 250" are tapered toward one end; however, the shared edge 275 may be horizontal in some forms. The arrangement shown, may be termed "alternating CD nesting." Such processing of the absorbent core web 200 can eliminate scrap with regard to the absorbent core web 200.

Regardless of the arrangement of the discrete cores on the web, as noted previously, the disparate lengths of the discrete absorbent cores can be noticeable to the user of disposable absorbent articles and can create a negative perception amongst users of the disposable absorbent articles incorporating such disparate length absorbent cores. For example, where disparate length absorbent cores are provided in a single package, consumer may get an impression of a lower quality article with little to no quality control.

However, in order to counter this negative perception, end edges of the absorbent cores which incorporate edges of the absorbent core web can be patterned. The shaping of the discrete absorbent cores, particularly in the areas where the absorbent core web edges are utilized, can decrease the negative perception generated by the disparate lengths of the absorbent cores. Referring to FIGS. 3A-3D, discrete absorbent cores 300 of the present disclosure may comprise a longitudinal centerline 380 and a lateral centerline 390 which is generally perpendicular to the longitudinal centerline 380 and in the same plane as the discrete absorbent core 300. The longitudinal centerline 380 bisects a first end width 373 and a second end width 377 discussed hereafter.

The absorbent core 300 further comprises a first longitudinally extending side edge 384 and a second longitudinally extending side edge 388. As shown, the first side edge 384 and the second side edge 388 may, in some forms, be generally inclined with respect to the longitudinal centerline 380. In some forms, the first longitudinal edge 384 and the second longitudinal edge 388 may be generally parallel to the longitudinal centerline 380. The absorbent core 300 further comprises a first end edge 394 connecting the first longitudinal edge 384 and the second longitudinal edge 388 and an opposing second end edge 398 connecting the first longitudinal edge 384 and the second longitudinal edge 388.

As shown, the discrete absorbent core 300 may be asymmetric about the lateral centerline 390, in some forms. In some forms, the discrete absorbent core 300 may be symmetric about the lateral centerline 390. In some forms, the discrete absorbent core 300 may be asymmetric about the longitudinal centerline 380. In some forms, the discrete absorbent core 300 may be symmetric about the longitudinal centerline 380. In some forms, the discrete absorbent core 300 may be asymmetric about the longitudinal centerline 380 and the lateral centerline 390.

The discrete absorbent cores 300 of the present disclosure may further comprise a variable length as mentioned previously. The length 375 extends from the first end edge 394 to a second end edge 398. The length of the discrete absorbent cores 300 may vary from size to size. For example, the discrete absorbent cores may vary from about 218 mm to about 318 mm, specifically including all values within this range and any ranges created thereby. And, because of the variable width of the absorbent core web, as mentioned previously, a few additional millimeters may be added on to the range. For example, for a target length of 218 mm, some of the absorbent cores may have a length of about 208 mm, 212 mm, 214 mm, or 216 mm. In such forms, a knife roll may be configured such that the absorbent cores do not exceed 218 mm, for example. In such forms, the absorbent web, at least in some portions may be wider than 218 mm. In those portions, the discrete absorbent cores would essentially be cut out of the web and no portion of the discrete absorbent core would be formed by an edge of the absorbent core web.

However, additional forms are contemplated where the knife roll is configured to allow the edges of the absorbent core web to form a portion of the end edges of each of the discrete absorbent cores. In such forms, for a target length of about 218 mm, the lengths of the discrete absorbent cores may vary from about 208 mm to about 228 mm, specifically reciting all values within these ranges and any ranges created thereby.

Similarly, for those discrete absorbent cores having a target length of 318 mm, some of the absorbent cores may have a length which is less than 318 mm, e.g. 308 mm. For those forms where the knife allows for the edges of the absorbent core web to form at least a portion of the first end edge and second end edge, the lengths of the absorbent cores may range from about 308 mm to about 328 mm, specifically reciting all values within these ranges and any ranges created thereby.

Regardless of the absorbent core target length, the variability in the absorbent core web can create absorbent cores having variable lengths. For example, absorbent cores having a target length of about 218 mm may be associated with absorbent articles designated as size 1, absorbent cores having a target length of about 248 mm may be associated with absorbent articles designated as size 2, and absorbent cores having a target length of about 318 mm may be associated with absorbent articles designated as size 3. The length of the absorbent cores for size 1 absorbent articles may vary from package to package. So, as an example, a first package of absorbent articles may comprise absorbent articles having absorbent cores having a first length while a second package of absorbent articles comprises absorbent articles having absorbent cores having a second length. The first length and the second length may be different. The same can be true for size 2 and size 3 packages of articles. Namely, variable lengths of absorbent cores can be found in different packages of the same size articles.

Additionally, the discrete absorbent cores of the present disclosure may comprise, as noted previously, the first end width 373 and the second end width 377. As shown, the first end width 373 and the second end width 377 are generally parallel to the lateral centerline 390. The first end width 373 may correspond to a width of the absorbent core 300 which is proximate the first end edge 394. The second end width 377 may correspond to a width of the absorbent core 300 which is proximate the second end edge 398.

In some forms, the first end width 373 and the second end width 377 may be the same for each of the sizes of articles. In some forms, the first end width 373 and the second end width 377 may be the same for only a portion of the sizes, e.g. sizes 1 and size 2. In such forms, another portion of differing sized articles, e.g. sizes 3 and size 4, the first end width 373 may be less than the second end width 377. In some forms, the first end width 373 may be less than the second end width 377 for all sizes of article, e.g. sizes 1, 2, 3, 4, and 5. For those forms where the first end width 373 is the same as the second end width 377, theses widths may range from about 40 mm to about 85 mm, from about 53 mm to about 80 mm, or from about 56 mm to about 76, specifically including all values within these ranges and any ranges created thereby. For those forms where the first end width 373 is less than the second end width 377, the first end width 373 may be from about 50 percent to about 90 percent of the second end width 377, from about 63 percent to about 83 percent of the second end width 377, or from about 70 percent to about 75 percent of the second end width 377, specifically including all values within these ranges and any ranges created thereby. In one specific example, the first end width 373 may be about 56 mm and the second end width 377 may be about 76 mm.

Due to the variable length as discussed previously, the absorbent cores of the present disclosure utilize patterned edges. The inventors have surprisingly found that the use of patterned edges can reduce the negative perception generated by the variable absorbent cores lengths. For example, still referring to FIGS. 3A-3D, as shown, the first end edge 394 and/or the second end edge 398 may comprise a plurality of patterned portions. In some forms, the second end edge 398 may comprise one or more patterned portions. In some forms, the first end edge 394 may comprise one or more patterned portions. In some forms, both the first edge 394 and the second end edge 398 may comprise one or more patterned portions.

FIG. 3C shows the first end edge 394 comprising one or more patterned portions. As shown, the first end edge 394 may comprise a first patterned portion 394A, a second patterned portion 394B and a connecting portion 394C disposed between and connecting the first patterned portion 394A and the second patterned portion 394B. The first patterned portion 394A may extend from the first longitudinal side edge 384, and the second patterned portion 394B may extend from the second longitudinal side edge 388. The connecting portion 394C connects the first patterned portion 394A and the second patterned portion 394B.

As shown, in some forms, the patterned portions 394A and 394B may comprise a plurality of scallops, e.g. a plurality of convex and concave curves in an alternating fashion. Each of the patterned portions 394A and 394B comprises a plurality of direction changes or inflection points. An inflection point is a point of a curve at which a change in the direction of curvature occurs. Inflection points may be determined by the K-Curvature Analysis method described herein. In some forms, the second patterned portion 394B may comprise a mirror image of the inflection points of the first patterned portion 394A. In some forms, the connecting portion 394C may be arcuate in nature. However, in some forms, the connecting portion 394C may be a straight line.

Figure 3A:
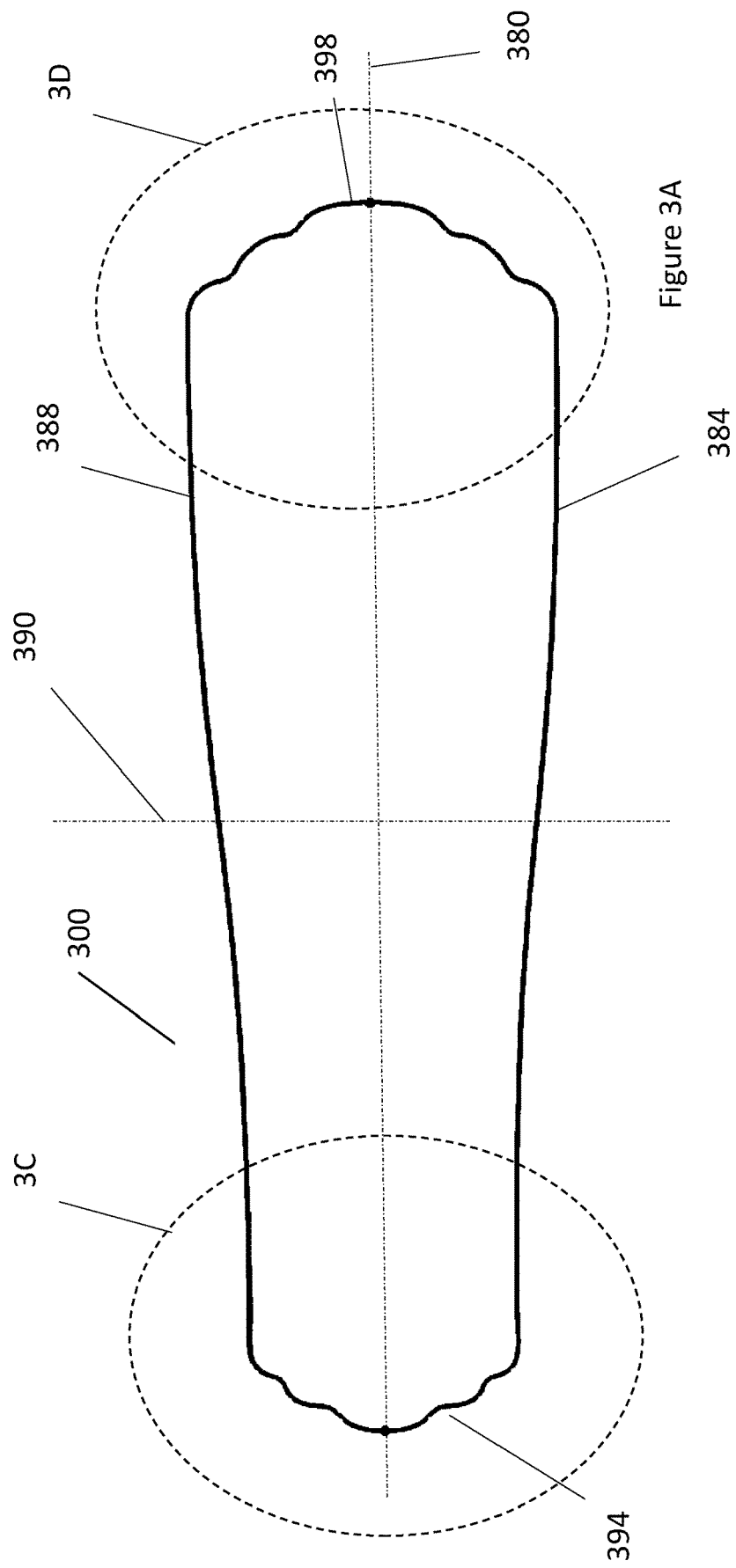
FIG. 3A is a plan view showing a discrete absorbent core in accordance with the present disclosure.
Figure 3B:
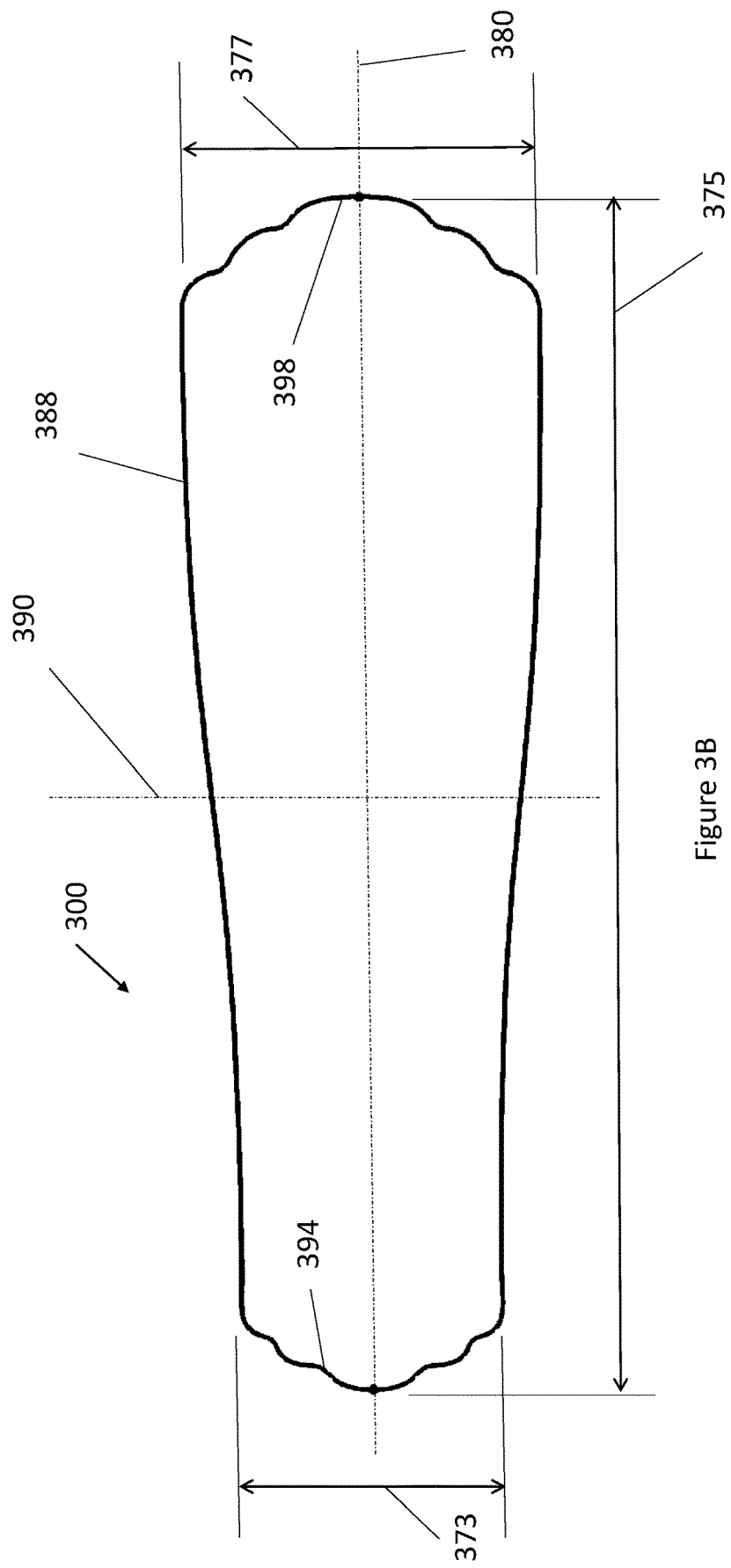
FIG. 3B is a plan view showing another discrete absorbent core in accordance with the present disclosure.
Figure 3D:
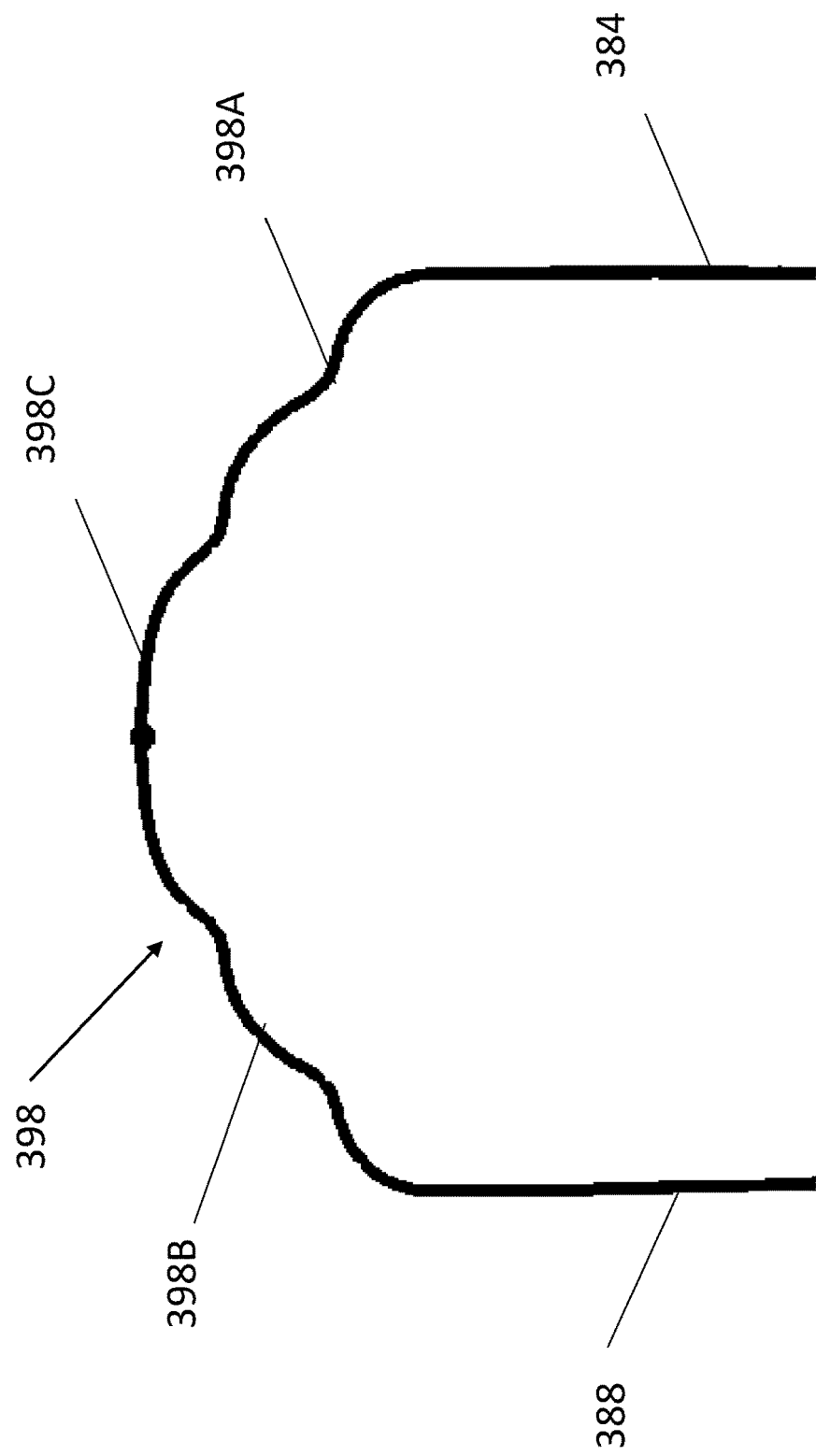
FIG. 3D is a close up view showing a second end of the discrete absorbent core of FIG. 3A encircled as 3D.

FIG. 3D shows the second end edge 398 comprising one or more patterned portions. As shown, the second end edge 398 may comprise a first patterned portion 398A, a second patterned portion 398B, and a connecting portion 398C disposed between and connecting the first patterned portion 398A and the second patterned portion 398B. The first patterned portion 398A may extend from the second longitudinal side edge 384, and the second patterned portion 398B may extend from the second longitudinal side edge 388. The connecting portion 398C connects the first patterned portion 398A and the second patterned portion 398B.

As shown, in some forms, the patterned portions 398A and 398B may comprise a plurality of scallops, e.g. a plurality of convex and concave curves in an alternating fashion. Each of the patterned portions 398A and 398B comprises a plurality of direction changes or inflection points. The first patterned portion 398A may comprise a mirror image of the inflection points of the second patterned portion 398B. In some forms, the connecting portion 398C may be arcuate in nature. However, in some forms, the connecting portion 398C may be a straight line. In some forms, the patterned portions of the first end edge 394 and/or the second end edge 398 may not extend laterally outboard of the longitudinal side edges 384, 388.

Figure 3E:
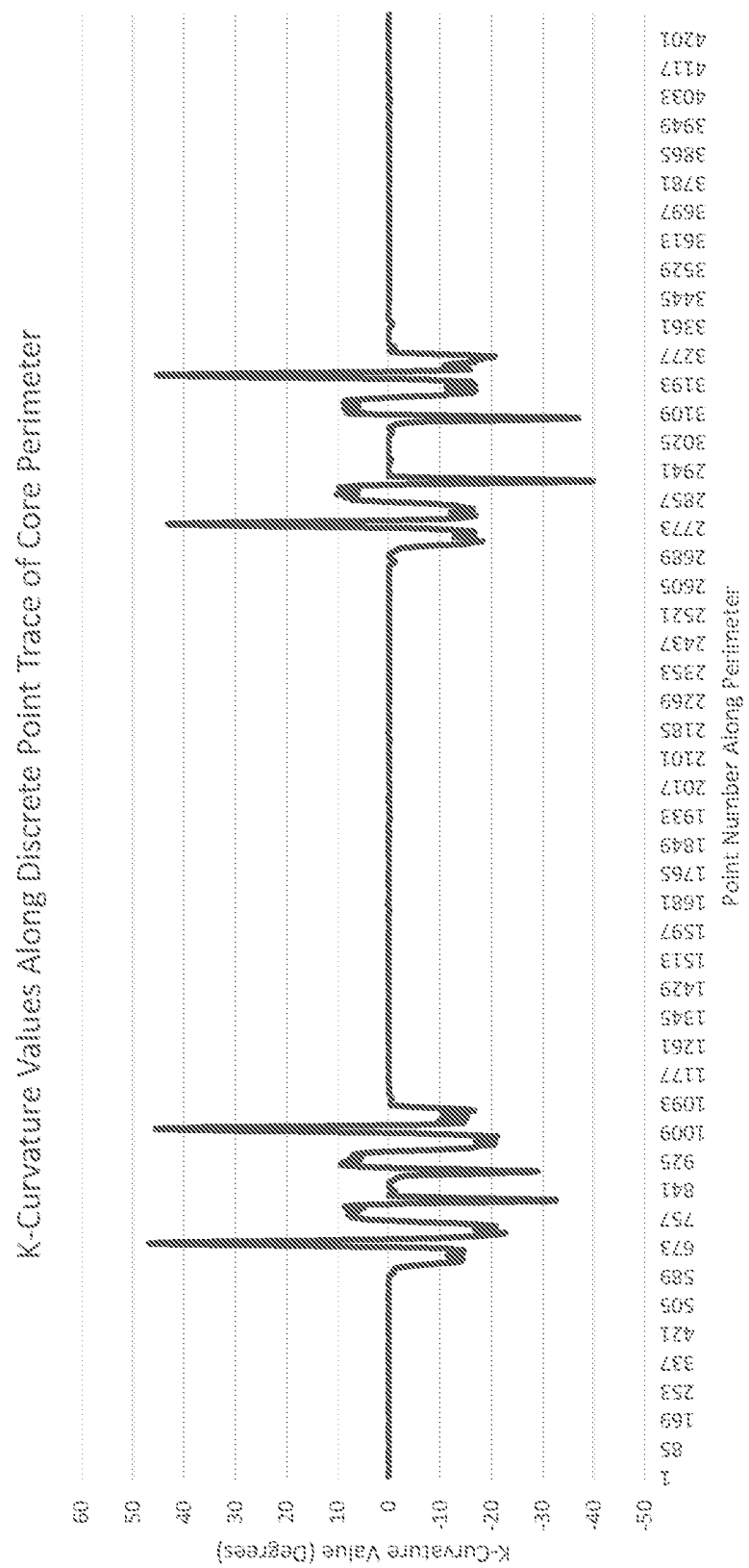
FIG. 3E is a graph showing a plurality of inflection points of an absorbent core of the present disclosure.

An exemplary inflection point graph is provided in FIG. 3E. An inflection point exists where there is a peak that is above or below +2 degrees or minus 2 degrees, respectively. As shown, moving from left to right on the graph, one end edge of an absorbent core (the first end edge) of the present disclosure, includes 10 inflection points. Similarly, the second end edge may comprise 10 inflection points. In some forms, either the first end edge or the second end edge may comprise at least four inflection points. In some forms, either the first end edge or the second end edge may comprise at least six inflection points. In some forms, either the first end edge or the second end edge may comprise at least eight inflection points. In some forms, either the first end edge or the second end edge may comprise at least 12 inflection points. While additional inflection points may be utilized, too many scallops or other designs can similarly create a negative perception. Accordingly, in some forms, either the first end edge or the second end edge may comprise less than about 14 inflection points.

Due to the variable width of the absorbent core web, in some forms the first end edge may comprise a first number of inflection points while the second end edge comprises a second number of inflection points. In some forms the first number of inflection points may be less than the second number of inflection points. In some forms, the first number of inflection points may be greater than the second number of inflection points. Additionally, similar to the variable lengths of the absorbent cores mentioned above, in some forms, absorbent cores associated with a particular size absorbent article may have a varying number of inflection points from package to package. For example, absorbent cores associated with a first package of absorbent articles may have an equal number of inflection points on the first edge and the second edge. In contrast, absorbent cores associated with a second package of absorbent articles may have a different number of inflection points on the first end edge compared to the second end edge. In such forms, the first package and the second package may be designated as the same size on the package, e.g. size 1. Or, the first package and the second package may be designated as different sizes.

Figure 4:
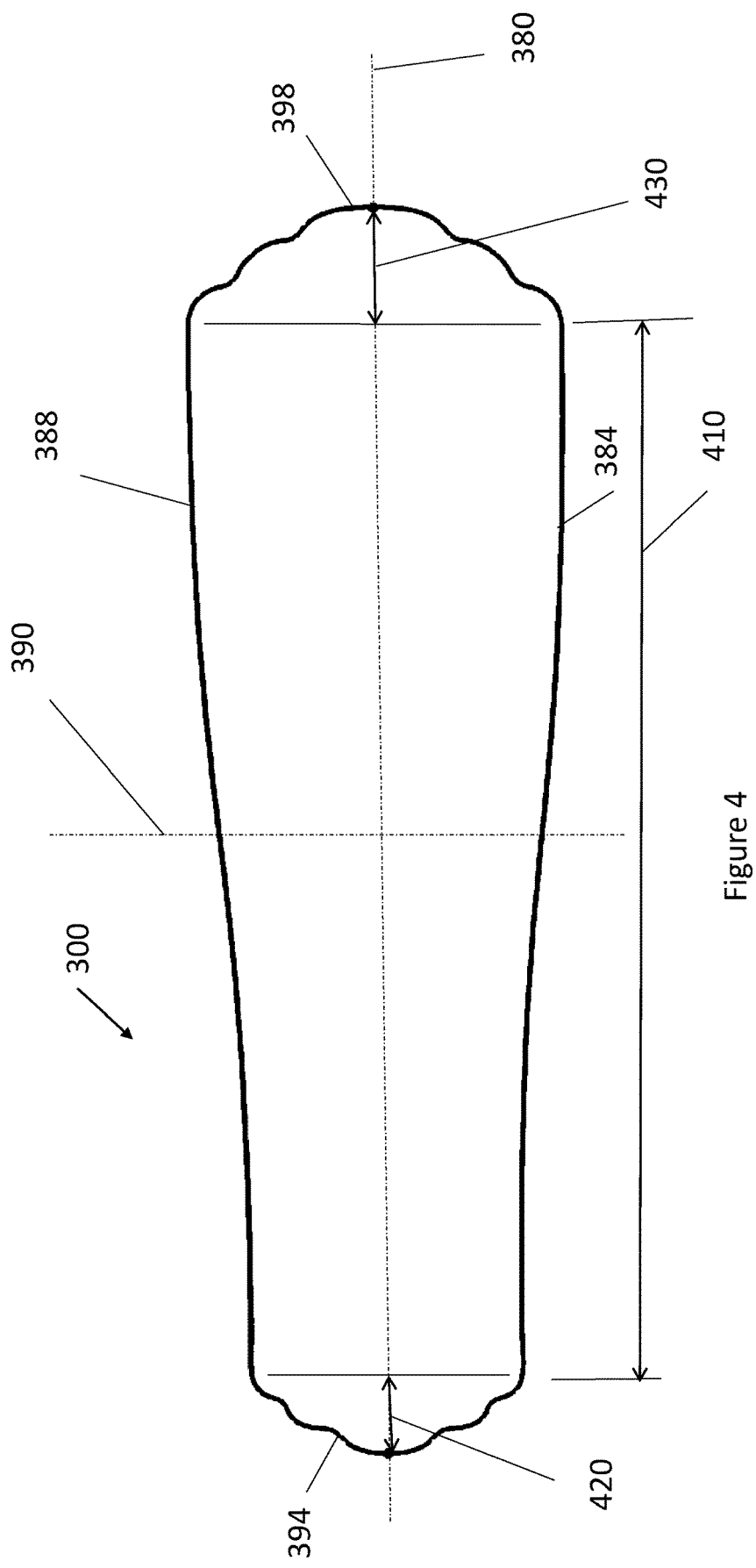
FIG. 4 is a plan view showing another discrete absorbent core in accordance with the present disclosure.

Additional features of the discrete cores of the present disclosure may be with regard to pattern distances 420 and 430 shown in FIG. 4. In some forms, the discrete absorbent cores 300 of the present disclosure, may comprise a body portion length 410 and a first pattern distance 420 corresponding to the first end edge 394 and a second pattern distance 430 corresponding to the second end edge 398. The first pattern distance 420 is measured from a first point to a second point. The first point is the intersection of the longitudinal centerline 380 and the first end edge 394. To determine the second point, a boundary line is drawn from the first longitudinal side edge 384 at the beginning of the first inflection point of the first end edge 394 proximate to the first longitudinal side edge 384 to the second longitudinal side edge 388 at the beginning of the first inflection point of the first end edge 394 proximate to the second longitudinal side edge 388. The second point is at the intersection of the longitudinal centerline 380 and the boundary line.

Similarly the second pattern distance 430 is measured between a first point and a second point. The first point is at the intersection of the longitudinal centerline 380 and the second end edge 398. To determine the second point, a second boundary line is drawn from the first longitudinal side edge 384 at the beginning of the first inflection point of the second end edge 398 proximate to the first longitudinal side edge 384 to the second longitudinal side edge 388 at the beginning of the first inflection point of the second end edge 398 proximate to the second longitudinal side edge 388. The second point is at the intersection of the longitudinal centerline 380 and the second boundary line.

The first pattern distance 420 plus second pattern distance 430 plus the body portion length 410 equals may be equal to the target length. As noted previously, the target length may vary by size. And due to the variability of the absorbent core web width the first pattern distance 420 and the second pattern distance 430 may vary as well. The first pattern distance 420 may vary from about 1 percent to about 3 percent of the overall length 375 (shown in FIG. 3B) of the absorbent core. Similarly, the second pattern distance 430 may vary from about 1 percent to about 3 percent of the overall length (shown in FIG. 3B) of the absorbent core. If the first pattern distance 420 and the second pattern distance 430 is too great, then the tapering of the absorbent core to their respective ends appears too gradual. If too small, then the patterned end edges may not be able to accommodate the variability in the absorbent core web and/or the cross direction tracking of the web during processing.

In some forms, the first pattern distance 420 may be from about 5 mm to about 28 mm, from about 8 mm to about 25 mm, or from about 15 mm to about 21 mm, specifically including all values within these ranges and any ranges created thereby. In some forms, the second pattern distance 430 may be from about 5 mm to about 28 mm, from about 8 mm to about 25 mm, or from about 15 mm to about 21 mm, specifically including all values within these ranges and any ranges created thereby. In some forms, the first pattern distance 420 may be less than or equal to 50 percent of the first end width 373. Similarly in some forms, the second pattern distance 430 may be less or equal to 50 percent of the second end width 377.

In some forms, the first pattern distance 420 and the second pattern distance 430 may be equal. In some forms, the first pattern distance 420 may be less than the second pattern distance 430. In such forms, the first pattern distance 420 may be about 5 mm less than the second pattern distance 430 or vice versa. If the difference is too great, this could negatively impact the visual appearance of the absorbent core to the consumer.

Other features which may be included in the discrete absorbent cores of the present disclosure pertain to the shape of the patterned edges. As discussed in additional detail below, a plethora of materials may be utilized in the absorbent cores of the present disclosure. The variety of materials can impact the how the absorbent cores react with regard to the patterning process. And the absorbent products into which these absorbent cores are placed, are subjected to a wide variety of stresses. For example, the absorbent core can experience a variety of stresses when being combined with the topsheet and/or backsheet. And in use, the absorbent cores can be exposed to additional stresses. These stresses can negatively impact the patterned edges of the absorbent cores if not properly designed.

Figure 5A:
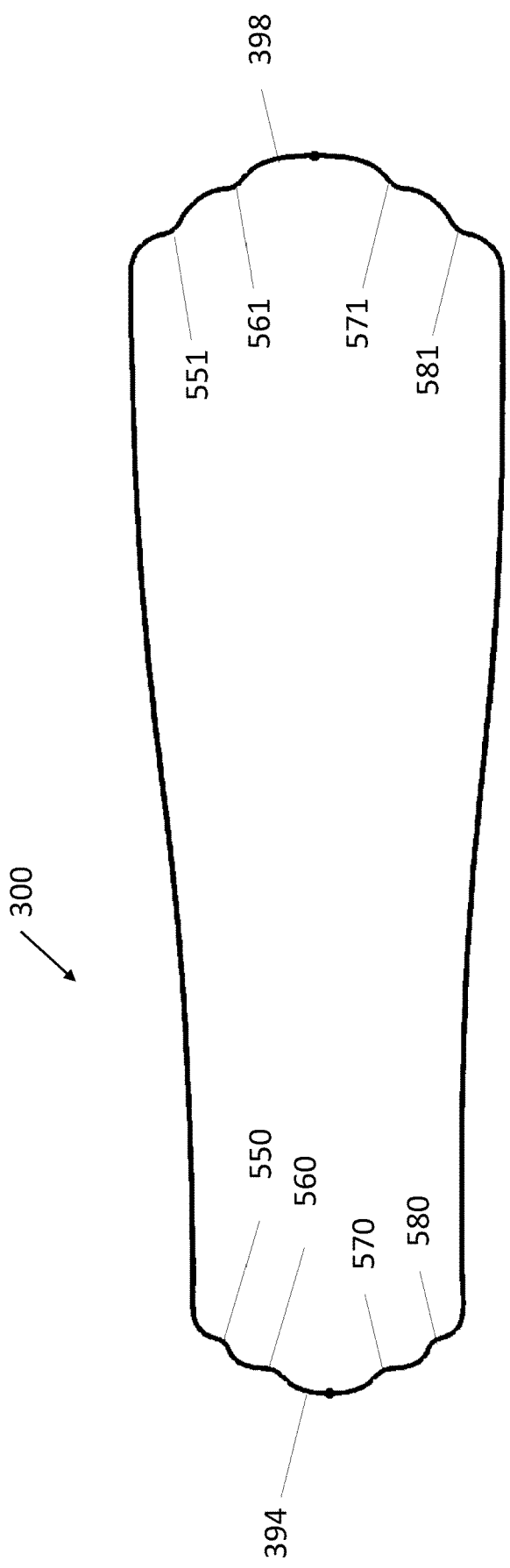
FIGS. 5A and 5B are plan views showing another discrete absorbent core in accordance with the present disclosure highlighting concave and convex portions, respectively.

Referring now to FIG. 5A, to accommodate the stresses to which the absorbent cores will be subjected to, in some forms, concave portions 550, 560, 570, and 580 on the first end 394 may have a radius which is less than the convex portions adjacent the concave portions 550, 560, 570, and 580. Similarly, concave portions 551, 561, 571, and 581 on the second end 398 may have a radius which is less than convex portions adjacent the concave portions 551, 561, 571, and 581. In some forms, the radius of the concave portions may be greater than about 0 mm. It is worth noting that with a 0 mm radius, stress concentration may occur at the intersection of two edges. While utilizing radii greater than 0 mm can reduce the stress concentration of the concave portions, too large a radius can be unappealing to the consumer. In some forms, the radii of the concave portions can be less than about 20 mm. In some forms, radii of the concave portions may be greater than about 0.5 mm, greater than about 1.0 mm, greater than about 1.5 mm, greater than about 2 mm, greater than about 5 mm, greater than about 10 mm, greater than about and less than about 20 mm, specifically reciting all values within these ranges and any ranges created thereby.

In some forms, the radii of the concave portions 550, 560, 570, and 580 can be less than the radii of the concave portions 551, 561, 571, and 581. In some forms, the radii of the concave portions 550 and 580 may be smaller than the radii for concave portions 560 and/or 570. In conjunction with the foregoing or independent therefrom, in some forms, the radii of the concave portions 551 and/or 581 may be smaller than the radii of the concave portions 561 and/or 571.

Figure 5B:
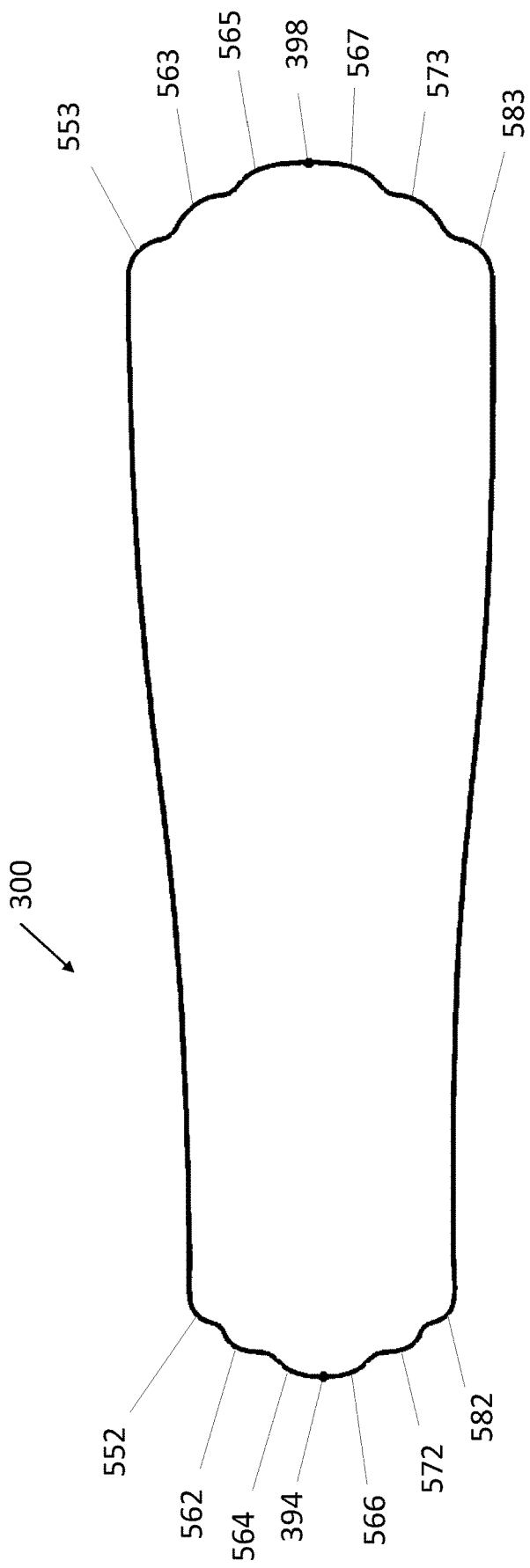

Referring now to FIG. 5B, convex portions 552, 562, 564, 566, 572, and 582 associated with the first end 394 may have a radius which is greater than about 4 mm and less than about 8 mm. Similarly, convex portions 553, 563, 565, 567, 573, and 583 associated with the second end 398 may have a radius which is greater than about 4 mm and less than about 8 mm.

As noted, the radii for the concave portions and the convex portions may be tied together in some forms. For example, a ratio of convex portion radii to concave portion radii may be from about 2 to 1, about 4 to 1, or about 5.3 to 1. In some forms, the ratio of convex portion radii to concave portion radii may be a first ratio for the first end 394 and a second ratio for the second end 398. In some forms, the first ratio may be less than the second ratio. In some forms, the second ratio may be less than the first ratio.

The number of convex portions on the first end 394 and the second end 398 can be important as well. If too few convex portions are included in the first end 394 and/or the second end 398, then the web width variations and cross direction tracking variations discussed herein may not be adequately addressed in all instances. And, at least in some of the absorbent cores processed, the end edges will appear as more of a quality/manufacturing defect than a purposeful cut. The inventors have found that the first end 394 and/or the second end 398 should have at least 4 convex portions.

In some forms, the first end 394 may comprise a different number of convex portions than the second end 398. For example, the first end 394 may comprise less convex portions than the second end 398.

Figure 6:
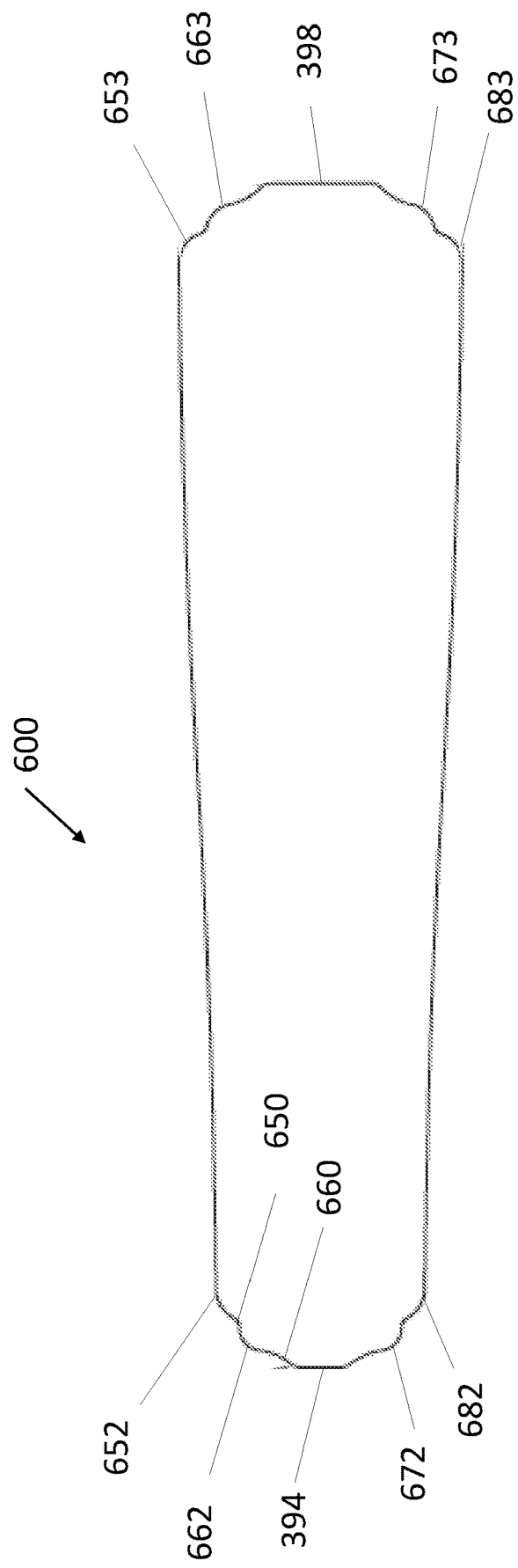
FIG. 6 is a plan view showing another discrete absorbent core in accordance with the present disclosure.

FIG. 6 depicts another form of an absorbent core 600 of the present disclosure. As shown, the discrete absorbent core 600 may comprise a plurality of concave portions 652, 662, 672, and 682 associated with the first end 394. Similarly, the second end 398 may comprise a plurality of convex portions 653, 663, 673, and 683. The radii associated with the convex portions of the absorbent core 600 may configured as discussed herein. And, concave portions of the absorbent core 600 may be configured as discussed herein. In some forms, concave portions 650 and 660 may be configured such that the concave portions have different radii. For example, in some forms, the exterior concave portion 650 may have a smaller radius than the interior concave portion 660. As another example, the exterior concave portion 650, in some forms, may have a larger radius than the interior concave portion 660. Concave portions associated with the second end 398 may be configured similarly or may have uniform radii, as noted previously.

Disposable Absorbent Articles

As discussed previously, disposable absorbent articles of the present disclosure may comprise a topsheet, a backsheet and an absorbent core disposed between the topsheet and the backsheet. In some forms, additional functional elements/layers may be disposed between the topsheet and the backsheet, as discussed below.

The absorbent articles of the present disclosure may comprise any known or otherwise effective topsheet, such as one which is compliant, soft feeling, and non-irritating to the wearer's skin. Suitable topsheet materials include a liquid pervious material that is oriented towards and contacts the body of the wearer permitting bodily discharges to rapidly penetrate through it without allowing fluid to flow back through the topsheet to the skin of the wearer.

A suitable topsheet can be made of various materials such as woven and nonwoven materials; apertured film materials including apertured formed thermoplastic films, apertured plastic films, and fiber-entangled apertured films; hydroformed thermoplastic films; porous foams; reticulated foams; reticulated thermoplastic films; thermoplastic scrims; film/nonwoven laminates, multi-layered nonwovens, e.g. spunbond-meltblown-spunbond material, or combinations thereof.

The topsheet may comprise tufts as described in U.S. Pat. No. 8,728,049 entitled "Absorbent Article Having a Tufted Topsheet" issued on May 20, 2014, U.S. Pat. No. 7,553,532 entitled "Tufted Fibrous Web" issued on Jun. 30, 2009, U.S. Pat. No. 7,172,801 entitled "Tufted Laminate Web" issued on Feb. 6, 2007, or U.S. Pat. No. 8,440,286 entitled "Capped Tufted Laminate Web" issued on May 14, 2013. The topsheet may have an inverse textured web as described in U.S. Pat. No. 7,648,752 entitled "Inverse Textured Web" issued on Jan. 19, 2010. Tufts are also described in U.S. Pat. No. 7,410,683 entitled "Tufted Laminate Web" issued on Aug. 12, 2008.

The topsheet may comprise one or more structurally modified zones as described in U.S. Pat. No. 8,614,365 entitled "Absorbent Article" issued on Dec. 24, 2013. The topsheet may have one or more out of plane deformations as described in U.S. Pat. No. 8,704,036 entitled "Sanitary Napkin for Clean Body Benefit" issued on Apr. 22, 2014. The topsheet may have a masking composition as described in U.S. Pat. No. 6,025,535 entitled "Topsheet For Absorbent Articles Exhibiting Improved Masking Properties" issued on Feb. 15, 2000.

The absorbent core is capable of absorbing or retaining liquids (e.g., menses and/or urine). The absorbent core may be manufactured from a wide variety of liquid-absorbent materials commonly used in sanitary napkins and other absorbent articles such as comminuted wood pulp which is generally referred to as airfelt. Examples of other suitable absorbent materials include creped cellulose wadding; melt-blown polymers including coform; chemically stiffened, modified or cross-linked cellulosic fibers; synthetic fibers such as crimped polyester or polyolefin fibers; peat moss; tissue including tissue wraps and tissue laminates; absorbent foams; absorbent sponges; superabsorbent polymers; absorbent gelling materials; or any equivalent material or combinations of materials, or mixtures of these. The absorbent core may have more than one layer wherein each layer may be identical or distinct in one or more property or composition from another layer.

In one particular form, the absorbent core structure may comprise a substrate and superabsorbent polymer layer as those described in U.S. Pat. No. 8,124,827 filed on Dec. 2, 2008 (Tamburro); US Patent Application Publication No. 2010/0228209, published on Sep. 9, 2010; US Patent Application Publication No. 2010/0262104, published on Oct. 14, 2010; or U.S. Pat. No. 8,674,169 issued on Mar. 18, 2014.

Forms are contemplated where at least one layer of the absorbent core may comprise superabsorbent polymers, a mixture of superabsorbent polymers and air felt, only air felt, and/or a high internal phase emulsion foam. In some instances, at least one layer of the absorbent core may comprise at least 80%, at least 85%, at least 90%, at least 95%, at least 99%, or up to 100% superabsorbent polymers, by weight of the absorbent material. In such instances, the at least one layer material may free of air felt, or at least mostly free of air felt.

In some forms, the absorbent core may comprise a heterogeneous mass comprising a fibrous web and one or more pieces of open cell foam intermixed within the fibrous web and/or enrobing one or more fibers within the fibrous web. In such forms, the absorbent core may be a two layer system wherein the upper layer is heterogeneous mass layer comprising one or more enrobeable elements and one or more discrete open-cell foam pieces. The upper layer heterogeneous mass layer may be a stratum as defined above. The lower layer may be an absorbent layer that comprises superabsorbent polymer. The absorbent core structure may comprise additional layers below the absorbent layer that comprises superabsorbent polymer. Heterogeneous mass layers are described in additional detail in US Patent Application Publication Nos. 2015/0313770; 2015/0374561; and 2015/0335498.

The one or more discrete portions of foam pieces enrobe the enrobeable elements. The discrete portions of foam pieces are open-celled foam. In an embodiment, the foam is a High Internal Phase Emulsion (HIPE) foam. In an embodiment, one continuous piece of open cell foam may enrobe multiple enrobeable elements, such as, for example, the fibers that make up the upper layer of a nonwoven web. The heterogeneous mass layer contains one or more discrete open-cell foam pieces foams that are integrated into the heterogeneous mass comprising one or more enrobeable elements integrated into the one or more open-cell foams such that the two may be intertwined. HIPE foam and methods of making are described in additional detail in U.S. Pat. No. 5,149,720 (DesMarais et al), issued Sep. 22, 1992; U.S. Pat. No. 5,827,909 (DesMarais) issued Oct. 27, 1998; and U.S. Pat. No. 6,369,121 (Catalfamo et al.) issued Apr. 9, 2002.

Alternatively, rather than discrete portions of foam pieces as mentioned above, the absorbent core of the present disclosure may, in some forms, comprise an open-cell foam. In some forms, a suitable open-cell foam may be produced from the polymerization of the monomers having a continuous oil phase of a High Internal Phase Emulsion (HIPE). HIPE foams and their production were mentioned previously. Another suitable open-cell foam is polyurethane.

The backsheet is generally that portion of the absorbent article positioned proximate to the garment-facing surface of the absorbent core. The backsheet may be joined to portions of the topsheet, the absorbent core, and/or any other layers of the absorbent article by any attachment methods known to those of skill in the art. The backsheet prevents, or at least inhibits, the bodily exudates absorbed and contained in the absorbent core from soiling articles such as bedsheets, undergarments, and/or clothing. The backsheet is typically liquid impermeable, or at least substantially impermeable. The backsheet may, for example, be or comprise a thin plastic film, such as a thermoplastic film having a thickness of about 0.012 mm to about 0.051 mm Other suitable backsheet materials may include breathable materials which permit vapors to escape from the absorbent article, while still preventing, or at least inhibiting, bodily exudates from passing through the backsheet.

In addition to the topsheet, backsheet, and absorbent core, in some forms, disposable absorbent articles of the present disclosure may further comprise one or more acquisition materials intermediate the topsheet and the absorbent core. The acquisition materials are typically hydrophilic materials that providing significant wicking of bodily exudates. These materials may dewater the topsheet and quickly move bodily exudates into the absorbent core. The acquisition materials may comprise one or more nonwoven materials, foams, cellulosic materials, cross-linked cellulosic materials, air laid cellulosic nonwoven materials, spunlace materials, or combinations thereof, for example. Typically, the acquisition material may have a width and length that are smaller than the width and length of the topsheet. The acquisition material may be a secondary topsheet in the feminine pad context.

Forms are contemplated where the patterned edges are provided on the acquisition materials and/or the absorbent core. The patterns may be as described herein.

For those forms where the disposable absorbent articles of the present disclosure are sanitary pads, wings or flaps may additionally be included. For those forms where the disposable absorbent articles comprise diapers, barrier leg cuffs, fastening elements, belts elastic waistbands, landing zones, etc. may be included.

Test Methods

K-Curvature Analysis Method

The identification of inflection points and pattern distances is accomplished by analysis of the boundary outline of a shaped absorbent core. The analysis is performed by generating an x-y plot of discrete points that trace the perimeter of the core, and calculating a smoothed estimate of the angle created by a forward looking slope and a backward looking slope at each point along the boundary, known as the k-curvature value. The x-y plot of discrete points is generated on a grid with a resolution of 5 points/mm, with the longitudinal axis of the core aligned parallel to the x-axis.

The k-curvature of the boundary at a point $(y_l, x_l)$ can be estimated using the following equation:

$$k-\text{curvature value} = \tan^{-1}\left(\frac{y_{l+k} - y_l}{x_{l+k} - x_l}\right) - \tan^{-1}\left(\frac{y_l - y_{l-k}}{x_l - x_{l-k}}\right)$$

Where k is equal to 12 and 'tan$^{-1}$' is assumed to produce an output over a range of angles of 2π radians.

As this calculation is performed for each of the points of the boundary a series of angles measured in a clockwise direction is generated with a horizontal slope taken to be zero. Each of the k-curvature angle outputs are converted from radians to degrees.

The k-curvature value at each consecutive point along the boundary is plotted, with the k-curvature angle the y-axis value, with each of the points along the entire boundary numbered consecutively along the x-axis.

On the k-curvature value plot identify a threshold level of ±2 degrees, and count the number of separate positive and negative peak regions along the boundary of the first end edge of the core, and record this value as its number of inflection points. Repeat this procedure for the second end edge of the absorbent core, and record the number of its inflection points.

To measure a pattern distance identify the difference in x-values (horizontal distance) between the point where the first inflection point of the first end edge begins, which is defined as where the transition from the k-curvature values near zero along the longitudinal side edge of the core exceeds ±2 degrees, and the first end edge of the core. Record this distance to the nearest 0.1 mm as the first pattern distance. Repeat this procedure for the second end of the absorbent core, and record this distance to the nearest 0.1 mm as the second pattern distance.

All measures are performed on five substantially similar absorbent cores and reported as the statistical mean of the five values.

Linear Distances

Linear distances may be measured by any appropriate instrument that is calibrated and capable of a measurement to the nearest 0.1 mm Area measurements are made using the projected area of the article, as viewed orthogonally to the plane of the article length and width, in square millimeters to the nearest 0.1 mm$^2$.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A package of disposable absorbent articles, the package comprising:
    a first plurality of absorbent articles and a second plurality of absorbent articles, each of the first plurality of absorbent articles and the second plurality of absorbent articles comprising a topsheet; a backsheet; and an absorbent core disposed between the topsheet and the backsheet, wherein, each absorbent core has a first longitudinal side edge and a second longitudinal side edge, a first end edge connecting the first longitudinal side edge and the second longitudinal side edge on one end of the absorbent core, a second end edge connecting the first longitudinal side edge and the second longitudinal side edge on an opposing second end of the absorbent core, wherein each of the first end edge and the second end edge comprise a first patterned portion, a second patterned portion, and a connecting portion, wherein each of the first patterned portion and second pattern portion comprise a plurality of inflection points disposed inboard of the first longitudinal side edge and the second longitudinal side edge, as determined via a k-curvature analysis test method, wherein a first portion of absorbent cores is associated with the first plurality of absorbent articles and wherein each of the absorbent cores of the first portion has a first length and a second portion of absorbent cores is associated with the second plurality of absorbent articles and wherein each of the absorbent cores of the second portion has a second length, and wherein the first length and second length are different.

2. The package of absorbent articles of claim 1, wherein first patterned portion and second patterned portion of the first end edge comprises a first number of inflection points, wherein the first patterned portion and second patterned portion of the second end edge comprises a second number of inflection point, wherein the first number and the second number are equal.

3. The package of absorbent articles of claim 1, wherein first patterned portion and second patterned portion of the first end edge comprises a first number of inflection points, wherein the first patterned portion and second patterned portion of the second end edge comprises a second number of inflection point, wherein the first number is greater than the second number.

4. The package of absorbent articles of claim 1, wherein first patterned portion and second patterned portion of the first end edge comprises a first number of inflection points, wherein the first patterned portion and second patterned portion of the second end edge comprises a second number of inflection point, wherein the first number is less than the second number.

5. The package of absorbent articles of claim 1, wherein each of the absorbent cores comprises a first pattern distance corresponding to the first end edge and a second pattern distance corresponding to the second end edge, wherein the first pattern distance is equal to the second pattern distance.

6. The package of absorbent articles of claim 1, wherein each of the absorbent cores comprises a first pattern distance corresponding to the first end edge and a second pattern distance corresponding to the second end edge, wherein the first pattern distance is greater than the second pattern distance.

7. The package of absorbent articles of claim 1, wherein each of the absorbent cores comprises a first pattern distance corresponding to the first end edge and a second pattern distance corresponding to the second end edge, wherein the first pattern distance is less than the second pattern distance.

8. The package of absorbent articles of claim 1, wherein the first end width is between 50 percent to 90 percent of the second end width.

9. The package of absorbent articles of claim 1, wherein each of the absorbent cores have a first width associated with the first end of the absorbent core and a second width associated with the second end of the absorbent core, wherein the first width is less than the second width.

10. The package of absorbent articles of claim 9, wherein the second end width is about 76 mm.

11. The package of absorbent articles of claim 9 wherein the first end width is about 56 mm.

12. The package of absorbent articles of claim 1, wherein the first plurality of plurality of absorbent articles are in a second package and designated as absorbent articles are disposed in a first package and designated as a first size and the second a second size, and wherein the first size and the second size are the same.

13. The package of absorbent articles of claim 1, wherein the first end width is between 63 percent to 83 percent of the second end width.

14. The package of absorbent articles of claim 1, wherein the first end width is between 70 percent to 75 percent of the second end width.

\* \* \* \* \*